Figure 1:
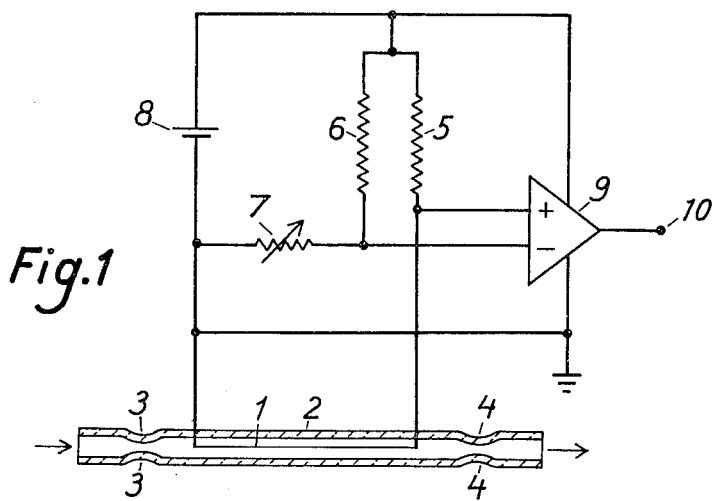

United States Patent [19]
Justi et al.

[11] 3,973,192
[45] Aug. 3, 1976

[54] DEVICE FOR PROVIDING AN EARLY DETECTION OF AEROSOL PRODUCTS OF COMBUSTION OF A POLYVINYL CHLORIDE SUBSTANCE

[75] Inventors: Eduard Wilhelm Leonhard Justi, Schapen; Henning Ewe, Braunschweig; Peter Wilhelm Reinhard Brennecke, Lehre, all of Germany

[73] Assignee: Telefonaktiebolaget L M Ericsson, Stockholm, Sweden

[22] Filed: Nov. 5, 1974

[21] Appl. No.: 520,969

[30] Foreign Application Priority Data
Nov. 28, 1973   Switzerland................... 160939/73

[52] U.S. Cl............................ 324/65 R; 324/65 P; 338/34
[51] Int. Cl.² ..................... G01R 27/02; H01C 7/00
[58] Field of Search............ 324/65 R, 65 P, 65 CR, 324/65 CP, 158 P; 338/34; 23/254 E; 73/23

[56]        References Cited
         UNITED STATES PATENTS
2,369,499   2/1945   Treuhaft............................ 324/65 P
3,820,958   6/1974   Cheng et al. ...................... 324/65 P OTHER PUBLICATIONS
Luc–Belmont, "Plastic Materials Not Giving off Poisonous Gas During Their Burning" Abstract of Fr. Patent 2165005, Sept. 7, 1973, Abstract No. 84212h Chem. Abstracts, vol. 80, No. 16, Apr. 22, 1974.
Kirk–Othmer, "Encyclopedia of Chemical Technology," vol. 12, Iron to Manganese, John Wiley & Sons, Inc., 1967, pp. 680.

*Primary Examiner*—John K. Corbin
*Assistant Examiner*—Wm. H. Punter
*Attorney, Agent, or Firm*—Hane, Baxley & Spiecens

[57]         ABSTRACT
A device for providing an early detection of aerosol products of combustion originating at least partly from a polyvinyl chloride substance. It comprises an electric resistance body of magnesium having a very small thickness and being arranged to be exposed to said aerosol products of combustion, an electric measuring circuit connected to the resistance body, and an indicating means arranged to generate an indicating signal in dependence on that the resistance of the resistance body exceeds a definite level.

5 Claims, 3 Drawing Figures

DEVICE FOR PROVIDING AN EARLY DETECTION OF AEROSOL PRODUCTS OF COMBUSTION OF A POLYVINYL CHLORIDE SUBSTANCE

The invention relates to a device for providing an early detection of aerosol products of combustion originating at least partly from a polyvinyl chloride substance.

A well-known problem with all heretofore used devices for detection of aerosol products of combustion, which devices employ for example a radioactive source and an ion detecting element or a source of light and a light detecting element as it is described more in detail in the Swedish patents Nos. 347,377 and 335,080, consists in that it is difficult to achieve an early detection of the aerosol products of combustion and at the same time maintain a good protection against false detections.

The device according to the invention offers a solution of said problem in the cases when the aerosol products of combustion at least partly originate from a polyvinyl chloride substance. The field of application for the invention is large as polyvinyl chloride substances today are present at the majority of the conceivable fire places in the form of insulating coverings on electric cables, floor coverings and so on.

Figures 2, 3:
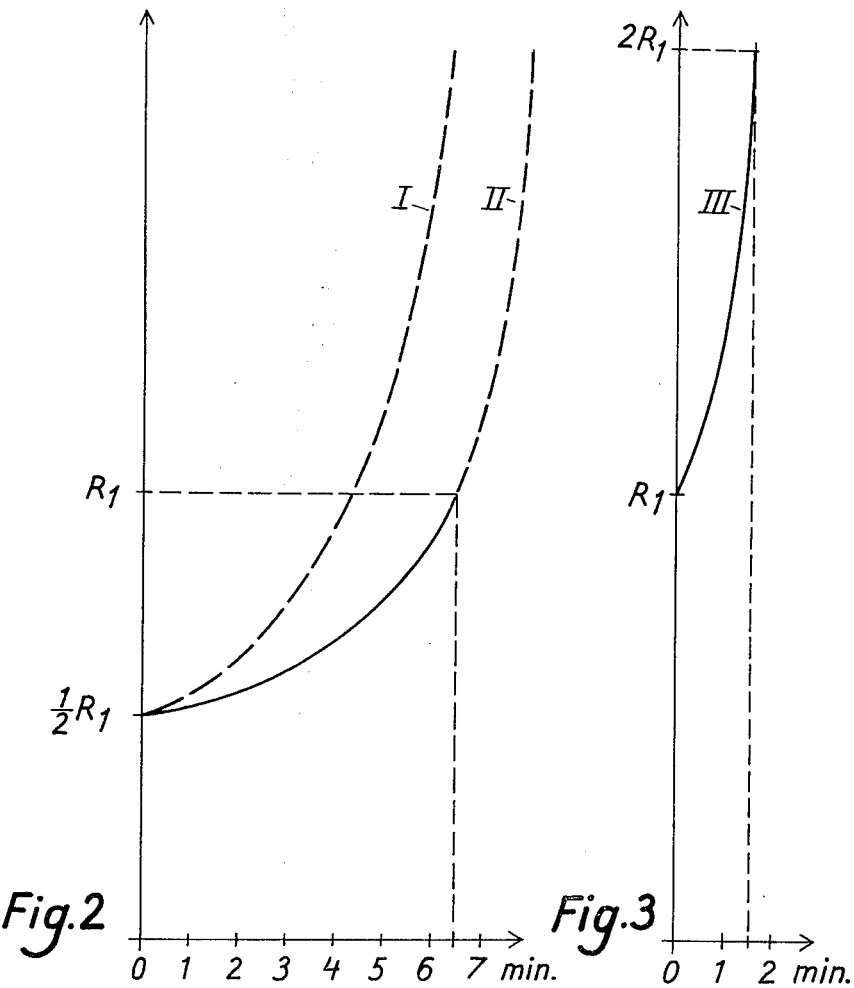

The device according to the invention, the characterizing features of which appear from the appended claims, will now be explained more in detail in connection with the enclosed drawing where FIG. 1 shows an electric circuit diagram over a preferred embodiment of the device according to the invention, and FIGS. 2 and 3 show time diagrams explaining the function of the device shown in FIG. 1.

FIG. 1 shows a preferred embodiment of the device according to the invention for providing an early detection of aerosol products of combustion originating at least partly from a polyvinyl chloride substance. A low-ohmic resistance body 1 of magnesium is provided with a relatively deep corrosion layer of magnesium dichloride and has the form of a 10 $\mu$m thick, 1 mm broad and 6 cm long foil which is freely mounted inside a plastic pipe 2. The plastic pipe 2, which has an inner width preferably <10 mm and according to the example = 2 mm, is with the help of a fan arrangement that is not shown in the figure arranged to achieve an air flow which surrounds the resistor body 1 and in which said aerosol products of combustion are expected to occur at fire. It is furthermore provided with concavely shaped depressions 3 and 4 at both sides of the resistance body 1 which concavenesses are adapted to limit the magnitude of the air flow achieved with the fan arrangement to 100 cm³ per minute.

The resistance body 1 is included in an electric measuring bridge, the other elements of which consist of two high-ohmic and equal resistors 5 and 6, a low-ohmic and variable resistor 7 whose resistance according to the example is in a normal state of the bridge adjusted to equal the double value of the resistance of the resistor body 1, and a voltage source 8. The bridge has two output electrodes which generate an output signal dependent on the resistance of the resistance body 1 and are connected to a pair of input poles of a differential amplifier 9. The differential amplifier which has a high gain and is energized from the voltage source 8 is in said normal state for the bridge arranged to generate a binary zero signal on an output 10.

The device according to the invention is based partly on the knowledge of two facts, namely that aerosol products of combustion which contain hydrochloric water steam, i.e. hydrochloric acid, are formed upon heating from 100°C and upwards of polyvinyl chloride substances, and that polyvinyl chloride substances today are present at the majority of the conceivable fire places in the form of insulating coverings on electric cables, floor coverings and so on, and partly on experiments which have shown that said aerosol products of combustion corrode a resistance body of magnesium in a fast auto-catalytic process implying that the effective cross section of the resistance body is reduced at an accelerating rate.

Curve I in FIG. 2 shows the variation of the resistance in time for the resistance body 1 in FIG. 1 such as it would be if said aerosol products of combustion would reduce the cross section of the resistance body 1 at a constant rate, while curve II shows the variation of the resistance in time for the resistance body 1 such as it actually has been measured on foils of 99.9 percent clean magnesium bought from Goodfellow Metals Ltd., Ruxley Towers, Claygate-Esher, Surrey, England. Curve II further shows how the relatively deep corrosion layer of magnesium dichloride specified for the resistance body 1 can be obtained by an ageing process at which a hydrochloric water steam flow is allowed to corrode the resistance body 1 during a few minutes until its resistance has increased to a value $R_1$ which is twice as great as the resistance value at the start of the ageing process.

Curve III in FIG. 3 shows that the ageing process provides a gain of about 75 percent of the time required to double the resistance of the resistance body 1. Accordingly, when said aerosol products of combustion occur and are conveyed to the resistance body 1 in FIG. 1 it may be expected that the resistance of the latter will within a short period of time exceed the adjusted resistance of the variable resistor 7 with the consequence that the differential amplifier 9 shifts its binary zero signal on the output 10 to a binary one signal which indicates that said aerosol products of combustion have been detected. From this it should be evident that the device according to the invention enables an early detection of fire when polyvinyl chloride substances occur at the fire place, especially as said aerosol products of combustion occur already at a temperature of 100°C. Experiments with the device according to the invention has further shown that it is comparatively insensitive for such air pollutions which normally are present. Summing up it appears to better combine an early detection of fire with a good protection against false detections than heretofore known fire detecting devices.

The device according to the invention can be modified in many ways within the scope of the appended claims. The resistance body 1 in FIG. 1 may for example consist of an insulating plate on which a very thin magnesium layer is precipitated preferably with a thickness within the interval 1–3 $\mu$m. Then said ageing process of course becomes quite unnecessary.

We claim:

1. Device for providing an early detection of aerosol products of combustion originating at least partly from a polyvinyl chloride substance, comprising an electric resistance body including a layer of magnesium dichloride arranged to be exposed to said aerosol products of combustion, an electric measuring circuit having two input electrodes connected to the resistance body and two output electrodes arranged to generate an output signal dependent on the resistance of said resistance body, and an indicating means connected to said output electrodes of the measuring circuit and arranged to generate an indicating signal when the resistance of the resistance body exceeds a predetermined level.

2. Device according to claim 1 wherein said layer is in the form of a foil having a thickness in the order of 10 $\mu$m.

3. Device according to claim 2, wherein the resistance body is freely mounted inside a pipe which has an inner diameter less than 10 mm and is arranged to provide an air flow surrounding the resistance body and in which said aerosol products of combustion are expected to occur.

4. Device according to claim 3, wherein said pipe has adjacent to opposite ends of the resistance body constrictions limiting the magnitude of said air flow to 100 $cm^3$ per minute.

5. Device according to claim 4 wherein said constrictions consist of concavely depressed wall portions of said pipe.

* * * * *